(12) United States Patent
Datta et al.

(10) Patent No.: US 9,447,435 B2
(45) Date of Patent: Sep. 20, 2016

(54) INTEGRATED PROCESSES FOR ANAEROBIC CONVERSION OF HYDROGEN AND CARBON OXIDES TO ALCOHOL

(71) Applicants: Rathin Datta, Chicago, IL (US); Steven G. Calderone, Chicago, IL (US); Jianxin Du, Naperville, IL (US); Robert Hickey, Okemos, MI (US)

(72) Inventors: Rathin Datta, Chicago, IL (US); Steven G. Calderone, Chicago, IL (US); Jianxin Du, Naperville, IL (US); Robert Hickey, Okemos, MI (US)

(73) Assignee: SYNATA BIO, INC., Warrenville, IL (US)

(*) Notice: Subject to any disclaimer, the term of this patent is extended or adjusted under 35 U.S.C. 154(b) by 0 days.

(21) Appl. No.: 14/176,035

(22) Filed: Feb. 7, 2014

(65) Prior Publication Data
US 2014/0227753 A1 Aug. 14, 2014

Related U.S. Application Data

(60) Provisional application No. 61/762,715, filed on Feb. 8, 2013.

(51) Int. Cl.
| | |
|---|---|
| *C12P 7/08* | (2006.01) |
| *C12P 7/16* | (2006.01) |
| *C12P 7/04* | (2006.01) |
| *C12P 7/06* | (2006.01) |

(52) U.S. Cl.
CPC ............ *C12P 7/04* (2013.01); *C12P 7/065* (2013.01); *C12P 7/08* (2013.01); *C12P 7/16* (2013.01); *Y02E 50/10* (2013.01); *Y02E 50/17* (2013.01); *Y02E 50/343* (2013.01); *Y02E 50/346* (2013.01)

(58) Field of Classification Search
None
See application file for complete search history.

(56) References Cited

FOREIGN PATENT DOCUMENTS

WO  WO 2011/139163  * 11/2011  ............ C12P 7/06

* cited by examiner

*Primary Examiner* — Karen Cochrane Carlson
*Assistant Examiner* — Jennifer M. H. Tichy
(74) *Attorney, Agent, or Firm* — Cardinal Law Group

(57) ABSTRACT

Integrated processes are disclosed for the anaerobic bioconversion of syngas to alcohol wherein a gas substrate of carbon monoxide, hydrogen and carbon dioxide is in contact with an aqueous menstruum that continuously contacts the gas substrate with said aqueous menstruum to produce alcohol and a depleted gas phase that is continuously withdrawn from the aqueous menstruum; continuously or intermittently and the gas substrate is made up of at least two gases having different compositions to provide an overall gas substrate having a ratio of electrons to carbon atoms in the range of about 5.2:1 to 6.8:1.

17 Claims, 1 Drawing Sheet

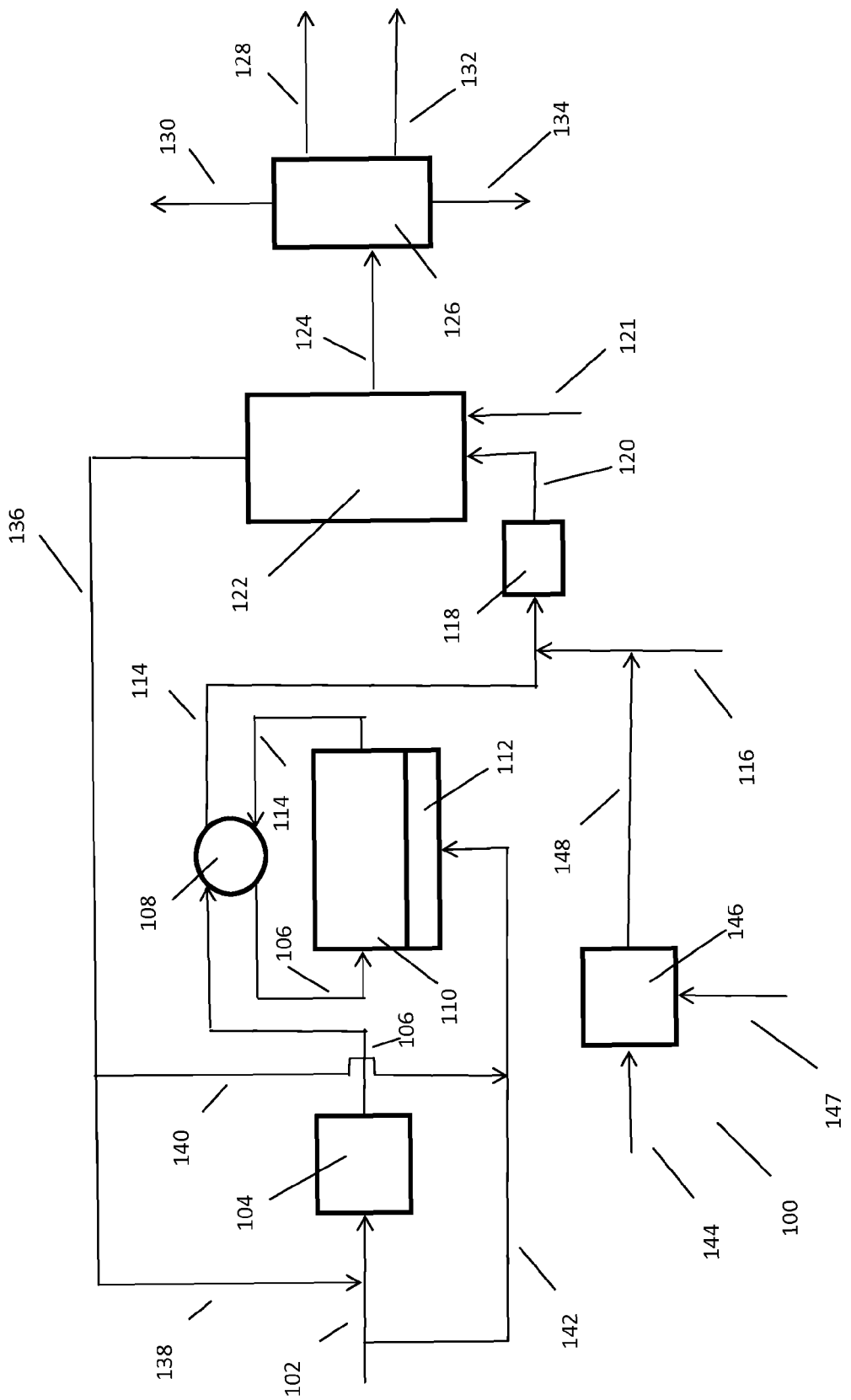

INTEGRATED PROCESSES FOR ANAEROBIC CONVERSION OF HYDROGEN AND CARBON OXIDES TO ALCOHOL

CROSS REFERENCE TO RELATED APPLICATIONS

Priority is claimed to U.S. provisional application Ser. No. 61/762,715, filed Feb. 8, 2013.

FIELD OF THE INVENTION

This invention pertains to integrated processes for anaerobic conversion of hydrogen and carbon oxides to alcohol especially ethanol, propanol and butanol.

BACKGROUND

Anaerobic fermentations of hydrogen and carbon monoxide involve the contact of the substrate gas in an aqueous fermentation menstruum with microorganisms capable of generating alcohols such as ethanol, propanol, i-butanol and n-butanol. The production of these alcohols requires significant amounts of hydrogen and carbon monoxide. For instance, the theoretical equations for the conversion of carbon monoxide and hydrogen to ethanol are:

$$6CO + 3H_2O \rightarrow C_2H_5OH + 4CO_2$$

$$6H_2 + 2CO_2 \rightarrow C_2H_5OH + 3H_2O.$$

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. For purposes herein, it is referred to as the hydrogen conversion.

Typically the substrate gas for carbon monoxide and hydrogen conversions is, or is derived from, a synthesis gas (syngas) from the gasification of carbonaceous materials, partial oxidation or reforming of natural gas and/or biogas from anaerobic digestion or landfill gas or off-gas streams of various industrial methods such as off gas from coal coking and steel manufacture. The substrate gas contains carbon monoxide, hydrogen, and carbon dioxide and usually contains other components such as water vapor, nitrogen, methane, ammonia, hydrogen sulfide and the like. (For purposes herein, all gas compositions are reported on a dry basis unless otherwise stated or clear from the context.)

These substrate gases are typically more expensive than equivalent heat content amounts of fossil fuels. Hence, a desire exists to use these gases efficiently to make higher value products. The financial viability of any conversion process, especially to commodity chemicals such as ethanol, will depend, in part, upon the costs of the feedstocks, conversion efficiency and operating and capital costs for generating the substrate gases; and upon the capital costs, the efficiency of conversion of the carbon monoxide and hydrogen to the sought products and the energy costs to effect the conversion of the substrate gases to the higher value products.

In a bioreactor, hydrogen and carbon oxides pass from the gas phase to dissolution in the aqueous menstruum, and then the dissolved hydrogen and carbon oxides contact the microorganisms for bioconversion. Due to the low solubilities of carbon monoxide and, especially, hydrogen in aqueous media, mass transfer can be a factor limiting rate and conversion in the bioconversion to alcohol. Therefore challenges exist in the design of commercial scale bioreactors that provide for the sought mass transfer while still enabling a high conversion of gas substrate at capital and operating costs that enable such a facility to be commercially competitive.

The off gases from bioreactors contain substrate that was not bioconverted and diluents such as methane and nitrogen. Although off gases can be recycled to the bioreactor or passed to another bioreactor, challenges can exist. For instance, the substrate gases may contain diluents that if recycled to a bioreactor, can build-up and reduce the partial pressure, thus reducing the driving forces for mass transfer of hydrogen and carbon monoxide to the aqueous menstruum.

Bell in United States published patent application No. 20100105118 discloses an integrated process for making alcohols which is said to provide high bioconversions of carbon monoxide in fermentations in the absence of oxygen. Bell notes at paragraph 0013 that in theory, carbon dioxide may be used as a reactant for the production of higher alcohols such as ethanol. However, he states that in practice the fermentation route to higher alcohols tends to be a net producer of carbon dioxide. In his disclosed process, the gas from the bioreactor which contains carbon dioxide is fed to a reaction section of a steam reformer. The reformer is either operated dry or with a mole ratio of water to carbon dioxide of less than 5:1. Bell states in paragraph 0025:

" . . . the integrated process of the present invention operates with a hydrogen excess and efficiently converts the carbon dioxide in the feed to the reforming process to carbon monoxide, and actually results in a lower process inventory of carbon dioxide."

Bell confirms the carbon dioxide net make of his process and the low conversion of hydrogen in the examples. In Example 1, 107 kmoles per hour of carbon dioxide are fed to the bioreactor and 194 kmoles of carbon dioxide are contained in the off gas from the bioreactor. Hydrogen is fed to the bioreactor at a rate of 318 kmoles per hour, and 231 kmoles per hour of hydrogen are contained in the off gas for a hydrogen conversion of about 28 percent. Similarly in Example 2, the feed to the bioreactor contains 25 kmole per hour of carbon dioxide, and 117 kmole per hour of carbon dioxide is contained in the off gas. Hydrogen is fed to the bioreactor at a rate of 298 kmole per hour with 206 kmole per hour of hydrogen passing to the off gas for a hydrogen conversion of about 31 percent. Bell subjects the off gas to a membrane separation unit operation to remove hydrogen to reduce the amount of hydrogen being passed back to the reformer. This hydrogen is fed to the hot box of the reformer as a portion of the fuel. See paragraphs 0074 and 0075.

Although Bell may have reduced carbon dioxide emissions as compared to the use of autothermal reforming or traditional steam reforming, the low conversion of hydrogen detracts from the commercial viability of the disclosed process.

Datta, et al., in United States Published Patent Application No. 20100105118 disclose processes for fermentation of syngas from indirect gasification using indirect gasification of biomass to produce a syngas and methane. The syngas contain methane is passed to a fermentation zone for conversion of the carbon monoxide and carbon dioxide and hydrogen to ethanol. The overhead from the fermentation zone is thus a methane-rich stream. This methane-rich stream is reformed to produce additional carbon monoxide and carbon dioxide and hydrogen that are passed to the fermentation zone. In the drawing, the off gas from the fermentation zone is subjected to membrane separation combined with a pressure swing adsorption to increase the concentration of methane, and then the reforming is conducted using a partial oxidation reformer.

Processes are therefore sought that can provide very high conversions of hydrogen and carbon monoxide in commercial-scale, continuous operations to alcohol.

SUMMARY

By this invention continuous processes are provided for the anaerobic conversion of hydrogen and carbon oxides to higher alcohols, especially ethanol, propanol and butanol, in which the anaerobic fermentation unit operations are integrated with unit operations to provide substrate gas and thereby enhance the efficiencies of bioconversion. In particular it has been found that the combination of high conversion and a specific range of $e^-/C$ ratio provides a surprising productivity to higher alcohols.

It has been found that the efficiency of hydrogen bioconversion in anaerobic processes depends not only on the presence of carbon dioxide in the aqueous fermentation menstruum but also the ratio of electrons to carbon atoms. The processes of this invention enable the use of advantageous syngas sources yet obtain enhanced conversion of the syngas by adjustment of the composition of the syngas by the addition of an additional gas. The adjustment in the composition by the addition of at least one other gas is particularly attractive because all hydrogen and carbon oxides values in the feed gases are available for the bioconversion. Moreover, compositional adjustments can be readily implemented on virtually a real time basis by the blend ratio. Hence, in the event that a unit operation generating syngas has an upset or other process change affecting syngas composition, the electron to carbon ($e^-/C$) ratio can be adjusted quickly to avoid undue loss of syngas values due to the use of less desirable electron to carbon atom ratios. Preferably the gas substrate being introduced into the bioreactor assembly comprises at least about 80, preferably at least about 90, mole percent of carbon monoxide, hydrogen and carbon dioxide.

In this aspect, continuous processes are provided for the anaerobic bioconversion of a gas substrate comprising carbon monoxide, hydrogen and carbon dioxide in an aqueous menstruum containing microorganisms suitable for converting said substrate to alcohol that comprise continuously contacting said gas substrate with said aqueous menstruum to bioconvert the gas substrate to alcohol and providing an alcohol-containing menstruum and a depleted gas phase; continuously withdrawing the depleted gas phase from said aqueous menstruum; continuously or intermittently withdrawing a portion of said menstruum for recovery of said alcohol, said withdrawal being sufficient to maintain the alcohol in said menstruum below a concentration that unduly adversely affects the microorganisms, wherein at least two gases having different compositions are used as the gas substrate, at least one of which has a high concentration of hydrogen such as syngas generated by steam reforming or coke oven gas and at least one other of which has a high concentration of carbon oxides, especially a high concentration of carbon dioxide, and can be admixed prior to contact with the aqueous menstruum or separately added to the aqueous menstruum to provide an overall, or cumulative gas substrate having a ratio of electrons to carbon atoms in the range of about 5.2:1 to 6.8:1, preferably between about 5.5:1 to 6.5:1, and most preferably between about 5.7:1 to 6.4:1. Preferably the gas having the high concentration of hydrogen (high hydrogen content gas) has an $e^-/C$ ratio of at least about 6:1, and the gas having the high concentration of carbon oxides (high carbon oxides content gas) has an $e^-/C$ ratio of 0:1 (e.g., containing carbon dioxide but not hydrogen or carbon monoxide) to about 5:1.

The fermentation is conducted in a bioreactor assembly containing one or more bioreactors. Any suitable bioreactor assembly may be used including but not limited to bubble column bioreactors; jet loop bioreactors; stirred tank bioreactors; trickle bed bioreactors; biofilm bioreactors; moving bed bioreactors; membrane bioreactors and static mixer bioreactors including, but not limited to, pipe bioreactors. A plurality of bioreactors in sequential gas flow may be desired where the substrate concentration in a bioreactor tends to be relatively uniform. The bioreactors need not, but can, provide a substantially uniform aqueous menstruum composition.

Preferably, the bioreactor assembly contains the aqueous menstruum for the anaerobic bioconversion said bioreactor assembly having at least one inlet portion and at least one gas outlet portion and at least one bioreactor in the bioreactor assembly is characterized as having a substantially uniform aqueous menstruum and a substantially non-uniform composition of the gas bubbles between the inlet portion and the outlet portion. Without wishing to be limited by theory, it is believed that this type of bioreactor assembly provides for sufficient driving force for hydrogen in gas bubbles to pass into the aqueous fermentation menstruum and thus facilitates obtaining high conversion efficiencies of hydrogen. The preferred processes use a deep tank bioreactor, most preferably a bubble column bioreactor. Advantageously, the electron to carbon ratios of the gas substrate to the bioreactor assembly result in a sufficiently low concentration of carbon monoxide in the gas substrate that carbon monoxide inhibition is not a factor in the operation of a bubble column bioreactor of the depth required to provide the sought conversions.

BRIEF DESCRIPTION OF THE DRAWINGS

FIG. 1 is a schematic depiction of an apparatus suitable for practicing certain broad aspects of the processes of this invention.

DETAILED DISCUSSION

All patents, published patent applications, and articles referenced herein are hereby incorporated by reference in their entirety.

Definitions

As used herein, the following terms have the meanings set forth below unless otherwise stated or clear from the context of their use.

The use of the terms "a" and "an" is intended to include one or more of the element described.

Alcohol means one or more alkanols containing two to six carbon atoms. In some instances the alcohol is a mixture of alkanols produced by the microorganisms contained in the aqueous menstruum.

Biogas means a gas produced from a renewable source of carbon and preferably containing at least about 20 mole percent carbon dioxide.

A bioreactor assembly is an assembly of one or more vessels suitable to contain aqueous menstruum and microorganisms for the bioconversion and can contain associated equipment such as injectors, recycle loops, agitators, and the like.

Anaerobically derived gas means biogas produced by the anaerobic digestion or fermentation of organic matter in the absence of oxygen and primarily contains methane and carbon dioxide.

Biomass means biological material living or recently living plants and animals and contains at least hydrogen, oxygen and carbon. Biomass typically also contains nitrogen, phosphorus, sulfur, sodium and potassium. The chemical composition of biomass can vary from source to source and even within a source. Sources of biomass include, but are not limited to, harvested plants such as wood, grass clippings and yard waste, switchgrass, corn (including corn stover), hemp, sorghum, sugarcane (including bagasse), and the like; and waste such as garbage and municipal waste. Biomass does not include fossil fuels such as coal, natural gas, and petroleum.

The term Component Composition means the composition of a gas where both water and nitrogen have been excluded from the calculation of the concentration of the components. As used herein, unless otherwise stated, compositions of gases are on an anhydrous basis and exclude the presence of nitrogen.

Electron to carbon ratio is calculated as the quotient of the quantity of two times the sum of the concentrations of carbon monoxide and hydrogen divided by quantity of the sum of the concentrations of carbon monoxide and carbon dioxide:

$$e^-/C = 2([CO]+[H_2])/([CO]+[CO_2]).$$

The abbreviation ppm means parts per million. Unless otherwise stated or clear from the context, ppm is on a mole basis (ppm (mole)).

Carbon monoxide inhibition means that microorganisms are adversely affected by a high concentration of dissolved carbon monoxide in the aqueous menstruum resulting in a significantly reduced, e.g., reduced by at least 15 percent, conversion of carbon monoxide or hydrogen per gram of active cells per liter, all other conditions remaining the same. A high concentration of dissolved carbon monoxide means that a higher conversion of carbon monoxide or hydrogen per gram of active cells per liter occurs at a lower dissolved concentration of carbon monoxide. The inhibitory effect may occur in a localized region in the aqueous menstruum; however, the occurrence of a carbon monoxide inhibition is typically observed by assessing the specific activity rate, i.e., the mass bioconsumed per mass of active microorganism per unit time, which under steady-state conditions can be approximated by the overall conversion for the volume of aqueous menstruum in the bioreactor. The concentration of carbon monoxide dissolved in the aqueous menstruum that results in carbon monoxide inhibition varies depending upon the strain of microorganism and the fermentation conditions.

Fossil carbonaceous materials, or fossil fuels, include, but are not limited to, natural gas; petroleum including carbonaceous streams from the refining or other processing of petroleum including, but not limited to, petroleum coke; and lignite and coal.

The terms "hydrocarbon-containing fuel" and "fuel" as used herein refer to fuels that contain hydrogen and oxygen atoms and may contain hetero atoms including, but not limited to oxygen and nitrogen atoms.

Aqueous menstruum, or aqueous fermentation menstruum, means a liquid water phase which may contain dissolved compounds including, but not limited to hydrogen, carbon monoxide, and carbon dioxide.

Intermittently means from time to time and may be at regular or irregular time intervals.

A concentration of the alcohol below that which unduly adversely affects the rate of growth of the culture of microorganisms will depend upon the type of microorganism and the alcohol. An unduly adverse effect on the growth rate means that a significant, usually at least a 20 percent, decrease in the growth rate of the microorganisms is observed in comparison to the growth rate observed in an aqueous menstruum having about 10 grams per liter alcohol therein, all other parameters being substantially the same.

Substantial uniformity in liquid phase means that composition of the liquid phase is substantially the same throughout a bioreactor. Usually the concentration of the alcohol is within about 0.2 mole percentage points in a uniform liquid phase.

Substantial non-uniformity in the gas phase means that the concentration (both in the gas bubbles and dissolved) of at least one component provided by the gas substrate changes by at least 50 percent between the point of entry of the gas into a bioreactor and the point that the gas emerges from the aqueous fermentation menstruum.

Deep tank bioreactor is a bioreactor having a depth of at least about 10 meters and can be operated to provide a substantial non-uniform substrate composition over the depth of the aqueous menstruum contained in the bioreactor. The term bubble column bioreactor as used herein refers to a deep tank bubble column bioreactor unless otherwise explicitly stated and include deep tank reactors where the gas is introduced as small bubbles to promote mixing. A commercial scale bioreactor has a capacity for aqueous menstruum of at least 1 million, and more preferably at least about 5, say, about 5 to 25 million, liters.

Stable gas-in-liquid dispersion means a mixture of gas bubbles in liquid where the bubbles predominantly flow in the same direction as the liquid currents in the bioreactor and may cause currents in the bioreactor, and the dispersion is sufficiently stable that it exists throughout the aqueous menstruum.

Syngas means a gas containing at least one of hydrogen and carbon monoxide and may, and usually does, contain carbon dioxide.

Coal gas has a typical composition of between about 3 and 8 volume percent carbon dioxide, about 20 to 35 volume percent carbon monoxide, about 12 to 25 volume percent hydrogen, and essentially the balance comprising nitrogen.

Coke oven gas has a typical composition of between about 1 and 5 volume percent carbon dioxide, about 3 and 10 volume percent carbon monoxide, about 20 and 40 volume percent methane, about 40 and 60 volume percent hydrogen with the balance being primarily nitrogen.

Anaerobic digester gas has a typical composition of between about 25 and 50 volume percent carbon dioxide and about 40 and 70 volume percent methane with small amounts of hydrogen, hydrogen sulfide, ammonia, and nitrogen.

Landfill gas has the typical composition of between about 35 and 60 volume percent carbon dioxide and about 35 and 60 volume percent methane with small amounts of carbon monoxide, hydrogen, hydrogen sulfide, oxygen, and nitrogen.

Steel mill gas has a composition of between about 30 and 85 volume percent carbon monoxide, about 10 to 40 volume percent carbon dioxide, and about 0 to 15 volume percent hydrogen. Nitrogen is generally present and may constitute up to about 30 volume percent of the steel mill gas. Other minor components are typically present.

Non-renewable gas stream means a gas derived from natural resources that takes at least a geologic age to replace once depleted and for this invention refers primarily to natural gas or methane stream derived fossil fuels.

Renewable sources or renewable carbon means a source of carbon that can be replaced in less than a millennium and in most cases in several years or less.

Natural gas means a combustible mixture of gaseous hydrocarbons from sedimentary rocks usually containing over 75% methane with minor amounts of 2-4 carbon alkanes.

Overview

The processes of this invention provide for high anaerobic bioconversion efficiencies of syngas to alcohol by using at least two gases to provide an overall substrate gas having certain electron to carbon ratios.

Syngas Generation

The processes of this invention use a combination of a high hydrogen content gas and a high carbon oxides content gas. The high carbon oxides content gas can be, but is not in the broadest aspects of the invention, a syngas. The high hydrogen content gas can be a syngas derived from steam reforming. Coke oven gas is another particularly attractive source of high hydrogen content gas. For the high hydrogen content gas, steam reforming is generally preferred due to the high hydrogen concentration of the produced syngas and the relative absence of contaminants that must be removed to prevent deleterious effects on the microorganisms for the anaerobic bioconversion to alcohol.

Gasification, partial oxidation, and reforming (autothermal and steam) of biomass or fossil carbonaceous materials are representative processes for generating syngas with higher carbon oxides contents. Gasification and partial oxidation processes are disclosed in copending United States Published Patent Application No. 20130137151. Rice, et al, in "Autothermal Reforming of Natural Gas to Synthesis Gas", Reference: KBR Paper #2031, Sandia National Laboratories, April 2007, discuss autothermal reforming and conditions. Steam reforming is a widely practiced commercial unit operation. See Logdberg, et al., "Natural Gas Conversion", Haldor Topsoe publication (undated). Reforming in the presence of carbon dioxide is known as carbon dioxide reforming with the partial pressure of carbon dioxide causing a shift in the product distribution of the reforming. See, for instance, Madsen, et al, "Industrial Aspects of $CO_2$-reforming", Paper No. 28f, presented at the AIChE Spring Meeting, Houston, Tex., March 1997. Reforming is a temperature dependent equilibrium reaction, and thus the addition of hydrogen, carbon monoxide or carbon dioxide will affect the distribution of steam, hydrogen, carbon monoxide and carbon dioxide from the fresh feed although the distribution in the produced syngas will be set by the thermodynamic equilibria.

Since the unit operations to make the syngas can vary widely, it is understood that the compositions of the syngas may similarly vary widely including the presence of components other than hydrogen, carbon monoxide and carbon dioxide, which components may be inert such as nitrogen and methane or components that may have to be removed due to potential adverse effects on the microorganisms such as hydrogen cyanide. Processes for removing adverse components include those disclosed in United States Published Patent Application Nos. 20130137151; 20130266997; and 20130337513; and U.S. Pat. Nos. 7,927,513 and 8,303,849. Also, the relative ratios among hydrogen, carbon monoxide and carbon dioxide may vary widely. An advantage of the processes of this invention is that such variations in the relative ratios can be accommodated to provide an overall, or combined, substrate gas to the bioreactor assembly that enables achieving a high conversion of hydrogen and carbon monoxide to alcohol.

In some preferred aspects of this invention, more than one source of syngas is used from different types of unit operations, e.g., a steam reformer and an autothermal reformer or partial oxidation unit or gasifier, to produce syngas so as to provide the desired substrate gas composition. The different types of unit operations may be parallel or may be sequential, i.e., the different unit operation to generate syngas occurs in the presence of syngas from another unit operation.

High carbon oxides content gases can be derived from syngas or other carbon dioxide. For instance, carbon dioxide can be added to meet the electron to carbon atom parameter desired for high conversion of hydrogen and carbon monoxide, and a significant amount of this additional carbon dioxide will be consumed in making the alcohol. Sources of the additional carbon dioxide can be derived directly or indirectly from biomass. One convenient source of relatively high purity carbon dioxide is from ethanol plants bioconverting carbohydrates to ethanol or other alkanols and diols.

Another source of high carbon oxides content gas is biogas such as from anaerobic digestion processes and from landfills. An advantage of the biogas is that it contains a significant amount of methane which can be used as, for instance, feedstock for a steam reforming unit operation or fuel within the process, e.g., for generating heat for distillation of the alcohol from the aqueous menstruum or for the hotbox of a steam reformer.

A yet further source of high carbon oxides content gas are effluent gases from combustions, e.g., exhaust from the hot box section of a steam reformer that is used to produce the high hydrogen content gas. Preferably the effluent gases from combustions are subjected to unit operations to selectively remove carbon dioxide as compared to, e.g., nitrogen, and other components that would be inert or deleterious to the fermentation. Examples of such unit operations, but are not limited to, are cyclic processes where carbon dioxide is removed by, e.g., amine extraction, alkaline salt extractions, water absorption, adsorptions/desorption, or physical absorption in organic solvents, and is thereafter released to provide a high carbon oxides content gas or membrane separation.

Table I provides typical compositions of the cumulative substrate gas fed to the bioreactor assembly using syngas from steam reforming.

TABLE I

| Component | Minimum | Maximum | Preferred Minimum | Preferred Maximum |
|---|---|---|---|---|
| Carbon Monoxide, mole % | 0 | 30 | 10 | 20 |
| Hydrogen, mole % | 30 | 75 | 50 | 70 |
| Carbon Dioxide, mole % | 2.5 | 50 | 10 | 15 |
| Methane, mole % | 0.1 | 30 | 0.3 | 10 |
| Nitrogen, mole % | 0 | 10 | 0 | 5 |
| Hydrogen cyanide, ppm(mole) | 0.001 | 2 | 0.001 | 0.01 |
| Other, ppm(mole) | 0.01 | 10000 | 0.01 | 10000 |

(Excluding water)

Alcohol, Microorganisms and Fermentation Conditions:

The alcohol or alcohols produced in the processes of this invention will depend upon the microorganism used for the fermentation and the conditions of the fermentation. One or more microorganisms may be used in the fermentation menstruum to produce the sought alcohol. Bioconversions of CO and H₂/CO₂ to propanol, butanol, ethanol and other alcohols are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds,. Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. Published Patent Application 20070275447, entitled "Indirect or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogemum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 U.S. Pat. No. 8,143,037.

Suitable microorganisms for bioconversion of syngas to alcohol generally live and grow under anaerobic conditions, meaning that dissolved oxygen is essentially absent from the fermentation liquid. Adjuvants to the aqueous menstruum may comprise buffering agents, trace metals, vitamins, salts etc. Adjustments in the menstruum may induce different conditions at different times such as growth and non-growth conditions which will affect the productivity of the microorganisms. U.S. Pat. No. 7,704,723 discloses the conditions and contents of suitable aqueous menstruum for bioconversion CO and $H_2/CO_2$ using anaerobic microorganisms.

Anaerobic fermentation conditions include a suitable temperature, say, between 25° and 60° C., frequently in the range of about 30° to 40° C. The conditions of fermentation, including the density of microorganisms, aqueous menstruum composition, and syngas residence time, are preferably sufficient to achieve the sought conversion efficiency of hydrogen and carbon monoxide and will vary depending upon the design of the fermentation bioreactor and its operation. The pressure may be subatmospheric, atmospheric or super atmospheric, and is usually in the range of from about 90 to 1000 KPa absolute and in some instances higher pressures may be desirable for biofilm fermentation bioreactors. As most bioreactor designs, especially for commercial scale operations, provide for a significant height of aqueous menstruum for the fermentation, the pressure will vary within the fermentation bioreactor based upon the static head.

The fermentation conditions are preferably sufficient to effect conversion of at least about 85, preferably at least about 90, percent of the hydrogen in the substrate gas fed to the bioreactor assembly to alcohol. The ease and ability to achieve these high conversions is also dependent upon having the specified electron to carbon ratios and carbon dioxide partial pressures in the substrate depleted gas phase. For commercial operations, the fermentation operation preferably provides a total molar conversion of hydrogen and carbon monoxide in the substrate gas feed in the range of at least about 93, preferably at least about 97, mole percent.

The rate of supply of the gas feed under steady state conditions to a fermentation bioreactor is preferably such that the rate of transfer of carbon monoxide and hydrogen to the liquid phase matches the rate that carbon monoxide and hydrogen are bioconverted. The rate at which carbon monoxide and hydrogen can be consumed will be affected by the nature of the microorganism, the concentration of the microorganism in the aqueous menstruum and the fermentation conditions. As the rate of transfer of carbon monoxide and hydrogen to the aqueous menstruum is a parameter for operation, conditions affecting the rate of transfer such as interfacial surface area between the gas and liquid phases and driving forces are important.

For deep tank bioreactor assemblies, a combination of bubble size and duration of contact with the aqueous fermentation menstruum are necessary to achieve these high conversions. Preferably the substrate gas is introduced into the bioreactor in the form of microbubbles. Often the microbubbles have diameters in the range of 0.01 to 0.5, preferably 0.02 to 0.3 millimeter. Preferably the substrate gas is injection using a motive fluid. Variations in the motive liquid flow rate can be used to modulate the microbubble size and thus modulate the rate of transfer of carbon monoxide and hydrogen to the liquid phase. Moreover, the modulation provides microbubbles that provide a stable gas-in-liquid dispersion. The injectors may be jet mixers/aerators or slot injectors. Slot injectors are preferred, one form of which is disclosed in U.S. Pat. No. 4,162,970. These injectors operate using a motive liquid. The injectors, especially slot injectors, are capable of operating over a wide range of liquid and gas flow rates and thus are capable of significant turn down in gas transfer capability. The injectors are characterized as having nozzles of at least about 1, often about 1.5 to 5, say, 2 to 4, centimeters as the cross-sectional dimension in the case of jet injectors or as the smaller cross-sectional dimension in the case of slot injectors. The bubble size generated by the injectors will be influenced by, among other factors, the rate of liquid flow through the injector and the ratio of gas phase to liquid phase passing through the injector as well as characteristics of the aqueous menstruum itself including, but not limited to its static liquid depth. See also, United States Published Patent Application 20130078688. In some instances the microbubbles which form a less dense gas-liquid dispersion and any motive fluid used to generate the microbubbles, can facilitate liquid mixing in a bioreactor. If required to provide adequate contact time between the gas bubbles and the aqueous fermentation menstruum, more than one bioreactor may be used in gas flow series in the bioreactor assembly.

The bioreactor assembly may comprise one or more bioreactors which may be, with respect to gas flow, in parallel or in series flow. The bioreactor assembly preferably contains a bioreactor that is characterized as having a substantially uniform aqueous phase composition and a substantially non-uniform substrate concentration. Where more than one bioreactor is used in gas flow series, at least the terminal bioreactor in the series has this characterization. Representative of these types of bioreactors are bubble column bioreactors, stirred tank bioreactors where the stifling rate is below that which results in a substantially uniform gas composition (liquid and gas phase) in the bioreactor, and bioreactors having gas-lift riser section or sections.

Because of economy of capital cost and operation, deep tank bioreactors are preferred. The deep tank bioreactors, in order to provide the sought contact time with the bubbles have a depth of at least 10 meters with stirred tank bioreactors often requiring less of a depth since the stifling can cause the bubbles to remain in the aqueous menstruum for a greater duration of time than those in a bubble column bioreactor. Regardless of the type of deep tank bioreactor, especially where using microbubbles that promote a stable dispersion of bubbles in the aqueous menstruum, mixing currents exist that not only assure the relatively uniform aqueous phase composition but also increase the contact time between the gas bubbles and the aqueous menstruum.

Where deep tank bioreactors are used, the depth of the aqueous fermentation menstruum is often at least about 15, say, between about 20 and 30, preferably between about 20 and 25, meters. Significant depths can be used in the bubble column bioreactors without undue risk of carbon monoxide inhibition as the substrate gas compositions provide a relatively low partial pressure of carbon monoxide even with these significant depths of aqueous fermentation menstruum.

Where more than one bioreactor is used in gas flow series, the initial bioreactor may be of any suitable configuration including, but not limited to, bubble column bioreactors; jet loop bioreactors; stirred tank bioreactors; trickle bed bioreactors; biofilm bioreactors; moving bed bioreactors; membrane bioreactors and static mixer bioreactors including, but not limited to, pipe bioreactors.

Another preferred bioreactor for the bioreactor assembly is a membrane bioreactor. There are various versions of membrane bioreactors. A typical membrane bioreactor comprises a plurality of hollow fibers that provide contact of the fermentation liquid with the substrate gas.

A general arrangement of a membrane bioreactor is disclosed in U.S. Published Patent Application 20080205539 and a particularly preferred arrangement of a membrane bioreactor is disclosed in U.S. Pat. No. 8,329,456. These documents disclose, details of a membrane bioreactor including flow path arrangements, fiber compositions, and sizing. As shown therein the membrane bioreactor can be arranged in many different ways. Of most interest is the function of the membrane with respect to the fermentation liquid and the gas substrate.

United States Published Patent Application 20080205539 shows an arrangement where the microorganisms are retained as a biofilm on the membrane in direct contact with menstruum. The biofilm may on either side of the membrane. The gas substrate contacts the side of the membrane opposite the biofilm and permeates the membrane to contact the microorganisms that comprise the biofilm. The gas and the biofilm together with the menstruum may be on either side of membrane, but typically the biofilm and menstruum are on the outside of the membrane to prevent plugging.

U.S. Pat. No. 8,329,456 shows a preferred arrangement using an asymmetric membrane that retains the microorganisms in a macropore layer located on the outside of the membrane while the fermentation menstruum passes on the opposite side of the membrane and in contact with liquid control layer control layer of the membrane. The substrate flows in contact with the outside of the membrane and into direct contact with the microorganisms in the biopores.

U.S. Pat. No. 8,101,387 shows a method for sequencing bioreactors in serial flow. The above documents also show the typical construction of the membranes into elongated modules with the hollow fibers extending along the length of modules. The substrate then enters and leaves the modules through gas distribution and gas collection chambers that communicate with the inlets and outlets of the hollow fiber lumens.

Product Recovery:

The bioreactor assembly may have added from time to time or continuously one or more streams of water, nutrients or adjuvants, and microorganisms. A portion of the aqueous menstruum is withdrawn from time to time or continuously from the bioreactor for product recovery. Usually, the withdrawal is made at a point at the upper portion of the aqueous menstruum in the vessel. Product recovery can consist of known equipment arrangements for removal of residual cell material, separation and recovery of liquid products from the fermentation liquid, return of recovered fermentation liquid and purging of waste streams and materials. Suitable equipment arrangements can include filters, centrifuges, cyclones, distillation columns, membrane systems and other separation equipment. U.S. Pat. No. 8,211,679 shows an arrangement for a product recovery bioreactor that recovers an ethanol product from a bioreactor.

Drawings

A general understanding of the invention and its application may be facilitated by reference to the Figures. The Figures are not in limitation of the broad aspects of the invention.

FIG. 1 is a schematic depiction of an apparatus generally designated as 100 suitable for practicing the processes of this invention. FIG. 1 omits minor equipment such as pumps, compressors, valves, instruments and other devices the placement of which and operation thereof are well known to those practiced in chemical engineering. FIG. 1 also omits ancillary unit operations. The process and operation of FIG. 1 will be described in the context of the recovery and production of ethanol. The process is readily adaptable to making other alcohols such as i-butanol, n-butanol, and n-propanol.

For purposes of discussion, natural gas will be used for providing the syngas for use in apparatus 100. It should be recognized that other carbonaceous sources can be used to provide syngas. The primary conversion process depicted is steam reforming. Natural gas is supplied via line 102 and passed to pretreatment assembly 104. Pretreatment assembly 104 typically is adapted to remove sulfur compounds from the natural gas. In some instances, pretreatment assembly 104 is encompassed within a steam reforming unit operation.

The natural gas having its sulfur content reduced is passed via line 106 to heat exchanger 108 and then to steam reformer 110. Steam reformer 110 converts the hydrocarbons in the natural gas to a syngas containing hydrogen, carbon monoxide and carbon dioxide. Lower pressure operations of steam reformer 110 provide less methane breakthrough then at higher pressure operations. Accordingly, for purposes of discussion, a lower pressure steam reforming unit operation is used, and the syngas contains about 75 mole percent hydrogen, about 18 mole percent carbon monoxide, about 5.5 mole percent carbon dioxide, and about 1.5 mole percent methane on and anhydrous basis.

The steam reforming is highly endothermic and hotbox 112 is provided to supply heat for the steam reforming. Syngas exits steam reformer 110 via line 114 which directs the syngas to heat exchanger 108 to preheat the incoming natural gas to steam reformer 110. After passing through heat exchanger 108, carbon dioxide is supplied to the syngas in line 114 via line 116 in an amount sufficient to adjust the electron to carbon ratio of the syngas to about 6.3:1 and provide the sought amount of carbon dioxide in the depleted gas phase (off gas) from the bioreactor assembly, usually a carbon dioxide partial pressure of at least about 2.5 kPa. As shown, the combined syngas and carbon dioxide stream is subjected to treatment in syngas purification unit 118. The function of syngas purification unit 118 will depend upon the source of the syngas and carbon dioxide and serves to remove components that may be adverse to the microorganisms used for the anaerobic fermentation of the syngas to ethanol such as hydrogen cyanide, ethylene, and acetylene. Syngas purification unit 118 is optional, and thus using syngas from a steam reformer and carbon dioxide from an ethanol plant, is not essential for the process depicted in FIG. 1.

The combined syngas and carbon dioxide stream (substrate gas) is passed from syngas purification unit 118 to bioreactor assembly 122 via line 120. For purposes of discussion, bioreactor assembly 122 comprises a plurality of deep tank bubble column bioreactors, one of which is shown in the drawing. Each deep tank bioreactor contains an aqueous fermentation menstruum having a depth of about 20 meters. The substrate gas is introduced at the bottom of the bioreactor in the form of finely dispersed microbubbles, e.g., using a slot eductor. The duration of the microbubbles in the bioreactor is sufficient to bioconvert at least 90 percent of the hydrogen and at least 98 percent of the carbon monoxide.

Aqueous fermentation menstruum is continuously withdrawn from bioreactor assembly 122 via line 124. The withdrawn fluid is passed to a product recovery assembly generally designated by 126. Product recovery assembly 126 comprises a number of unit operations to remove solids, entrained gases and recover ethanol. Usually product recovery assembly 126 contains a distillation assembly to fractionate the withdrawn fluid into an ethanol product stream which is removed via line 128 and a water fraction which is removed via line 132. Centrifuges or other solid-liquid separation unit operations may be used to remove cells and other solid debris from the fluid prior to it being passed to the distillation assembly, or the fluid may be passed to the distillation assembly without the removal of solids with the solids being removed with the still bottoms. As shown, a solids-containing stream is removed from product recovery assembly 126 via line 134. The solids-containing stream may be directed to digesters to recover carbon and nutrient values. The withdrawn fluid will also typically include lower boiling components such as methane and hydrogen. These lower boiling components are shown as being removed from a product recovery assembly 126 via line 130. Due to the high efficiency of the processes of this invention, often the lower boiling components have a lower heating value and are sent to a flare for disposal.

Returning to a bioreactor assembly 122, make-up water to replenish aqueous menstruum removed for product recovery is provided via line 121. The make-up water may contain nutrients and other adjuvants for the anaerobic fermentation, and may also contain microorganisms for the bioconversion. Substrate depleted gas phase is emitted from the top of the aqueous fermentation menstruum in the bubble column bioreactor. The depleted gas phase contains about 3 volume percent carbon dioxide at substantially atmospheric pressure. The depleted gas phase is withdrawn from bioreactor assembly 122 via line 136. The depleted gas phase contains methane, hydrogen, carbon dioxide, and relatively little carbon monoxide and thus has value either as a supplement to the natural gas forced steam reforming or as a fuel for the steam reformer. As shown, the depleted gas phase in line 136 can be passed via line 138 to line 102 and then passed to pretreatment assembly 104. Since the depleted gas phase is derived from contact with the aqueous fermentation menstruum, it can contain sulfur compounds that were present in the aqueous menstruum as adjuvants for the microorganisms. The pretreatment assembly 104 serves to remove these sulfur compounds to provide a gas feed suitable for the catalytic steam reforming. In addition, or alternatively, depleted gas phase may be passed via line 140 to line 142 to supply natural gas to hotbox 112 for steam reformer 110. As shown, line 142 obtains the natural gas for hotbox 112 from line 102.

Carbon dioxide can be used to provide the desired electron to carbon ratio for the substrate gas as described above. Other sources of carbon dioxide can be used. FIG. 1 illustrates that a carbonaceous material can be passed via line 144 to gasification unit 146. Gasification unit 146 serves to gasify the carbonaceous material, e.g., wood, to generate a gas containing carbon dioxide, carbon monoxide and hydrogen. Considerable flexibility exists in the operation of gasification unit 146 to provide a desired mole ratio of carbon dioxide to hydrogen such that when combined with the syngas from steam reformer 110, the substrate gas has the desired electron to carbon ratio and carbon dioxide content. Syngas exits gasification unit 146 via line 148. Not shown, but often desirable, is using the syngas which is at a high temperature as a source of heat for indirect heat exchange with the natural gas being provided to steam reformer 110. The syngas is directed to line 116 where it is combined with the syngas from steam reformer 110 in line 114. Syngas purification unit 118 is typically used. Combined gases can contain aromatic, ethylenic, acetylenic and hydrogen cyanide components that are preferably substantially removed prior to introducing the substrate gas into bioreactor assembly 122.

In another embodiment illustrated in FIG. 1, a sequential syngas generation process is used to adjust the electron to carbon ratio of a syngas generated by steam reforming. As depicted, all or a portion of the syngas from steam reformer 110 is passed via line 114a to partial oxidation reactor 114b. Hydrocarbonaceous fuel (e.g., natural gas) for partial oxidation reformer 114b is supplied by line 114c and oxygen for the partial oxidation is provided by line 114d. The partial oxidation reactor is operated at a temperature above about 1400° C. and provides a reformate that exits via line 114e and returns to line 114 for heat exchange with the incoming natural gas for the steam reforming in heat exchanger 108.

The preamble to any claim in this invention is part of the entire claim and applies to interpreting the scope and coverage of each claim.

It is claimed:

1. A continuous process for the anaerobic bioconversion of a gas substrate comprising carbon monoxide, hydrogen and carbon dioxide in an aqueous menstruum containing microorganisms suitable for converting said substrate to alcohol, comprising:

continuously contacting said gas substrate with said aqueous menstruum to bioconvert gas substrate to alcohol and providing an alcohol-containing menstruum and a depleted gas phase;

continuously withdrawing the depleted gas phase from said aqueous menstruum;

continuously or intermittently withdrawing a portion of said menstruum for recovery of said alcohol, said withdrawal being sufficient to maintain the alcohol in said menstruum below a concentration that unduly adversely affects the microorganisms, wherein at least two gases having different compositions are used as the gas substrate to provide an overall gas substrate having a ratio of electrons to carbon atoms in the range between 5.2:1 to 6.8:1.

2. The process of claim 1 wherein at least one of said two gases is a coke oven gas or a syngas from steam reforming of hydrocarbonaceous gas.

3. The process of claim 2 wherein the other of said two gases is selected from the group of steel mill gas, syngas from gasification of carbonaceous material, syngas from partial oxidation of carbonaceous material, and synthesis gas from autothermal reforming of carbonaceous material.

4. The process of claim 1 wherein at least one of said two gases comprises at least about 25 mole percent carbon dioxide.

5. The process of claim 4 wherein the at least one of said two gases comprises biogas.

6. The process of claim 4 wherein the at least one of said two gases comprises landfill gas.

7. The process of claim 4 wherein the at least one of said two gases comprises anaerobic digester gas.

8. The process of claim 1 wherein at east two syngases are used to provide the overall gas substrate.

9. The process of claim 8 wherein the syngases are derived in parallel.

10. The process of claim 8 wherein the syngases are derived sequentially.

11. The process of claim 10 wherein a syngas from steam reforming is passed to a partial oxidation having a hydrocarbonaceous feed to provide an adjusted electron to carbon ratio.

12. The process of claim 1 wherein the overall gas substrate has a ratio of elections to carbon atoms in the range of about 5.5:1 to 6.5:1.

13. The process of claim 1 wherein the alcohol is derived from a fermentation having a conversion of at least about 85 mole percent of hydrogen and carbon oxides.

14. The process of claim 1 wherein the alcohol comprises ethanol.

15. The process of claim 1 wherein the alcohol comprises butanol.

16. The process of claim 1 wherein the bioreactor assembly comprises at least one of bubble column bioreactor; jet loop bioreactor; stirred tank bioreactor; trickle bed bioreactors; biofilm bioreactor; moving bed bioreactor; membrane bioreactor and static mixer bioreactor.

17. The process of claim 1 wherein at least one of the gases is a high hydrogen content gas having an electron to carbon ratio of at least about 6:1, and at least one other gas is a high carbon oxides content gas having an electron to carbon ratio of between 0:1 to 5:1.

* * * * *